United States Patent
Shannon

(10) Patent No.: US 6,537,247 B2
(45) Date of Patent: Mar. 25, 2003

(54) SHROUDED STRAIN RELIEF MEDICAL BALLOON DEVICE AND METHOD OF USE

(76) Inventor: Donald T. Shannon, 31881 Stonycreek Rd., Trabuco Canyon, CA (US) 92679

(*) Notice: Subject to any disclaimer, the term of this patent is extended or adjusted under 35 U.S.C. 154(b) by 9 days.

(21) Appl. No.: 09/873,577

(22) Filed: Jun. 4, 2001

(65) Prior Publication Data

US 2002/0183777 A1 Dec. 5, 2002

(51) Int. Cl.⁷ .............................................. A61M 31/00
(52) U.S. Cl. .................................. 604/103.05; 606/194
(58) Field of Search .......................... 606/192, 198, 606/108, 194; 623/99.01, 1.11; 604/103.05, 103.13, 103.14; 600/208

(56) References Cited

U.S. PATENT DOCUMENTS

| RE33,561 E | * | 3/1991 | Levy ........................ 428/36.92 |
| 5,087,246 A | | 2/1992 | Smith |
| 5,147,302 A | | 9/1992 | Euteneur |
| 5,158,548 A | * | 10/1992 | Lau et al. .................... 606/194 |
| 5,439,445 A | * | 8/1995 | Kontos ...................... 604/103.1 |
| 5,824,041 A | * | 10/1998 | Lenker et al. ............... 606/195 |
| 5,843,092 A | * | 12/1998 | Heller et al. ................. 606/108 |
| 5,876,374 A | * | 3/1999 | Alba et al. ............. 604/164.08 |
| 5,935,114 A | * | 8/1999 | Jang et al. ................... 604/264 |
| 6,264,671 B1 | * | 7/2001 | Stack et al. .................. 606/198 |
| 2001/0008970 A1 | * | 7/2001 | Ravenscroft et al. ........ 606/198 |

FOREIGN PATENT DOCUMENTS

WO    WO94/07561    4/1994

* cited by examiner

Primary Examiner—David O. Reip
Assistant Examiner—D Jacob Davis
(74) Attorney, Agent, or Firm—Intellepharm, Inc.; Manfred E. Wolff

(57) ABSTRACT

A dilation catheter device comprising a shroud tube having a total preselected diameter effective for use in a preselected body lumen, the shroud tube having a strain relief tube extending therethrough which is adapted to reversibly form a flared, funnel-shape and a collapsed shape for contacting the surface of a dilation balloon, whereby the configuration of the balloon can be altered by altering the position of contact of the distal end of the strain relief tube with the surface of the balloon. Methods for use of the device and articles of manufacture containing the device are also taught.

26 Claims, 2 Drawing Sheets

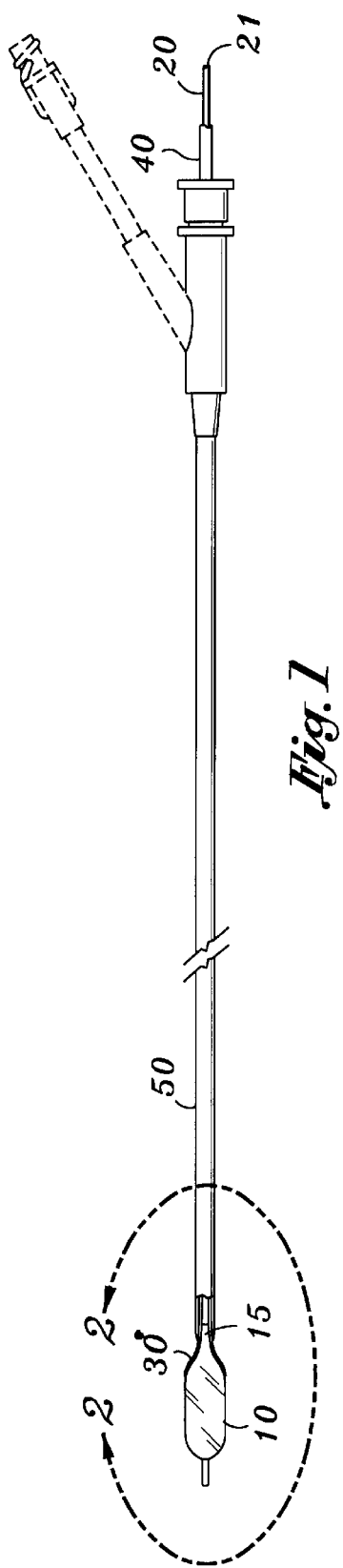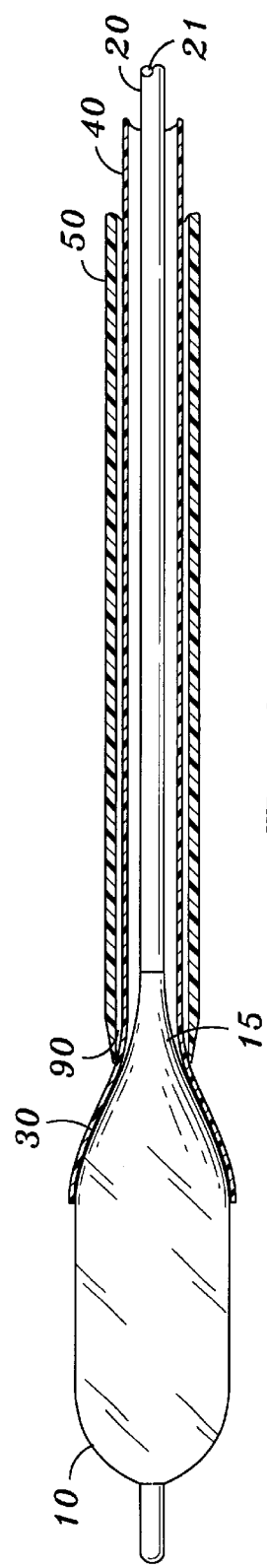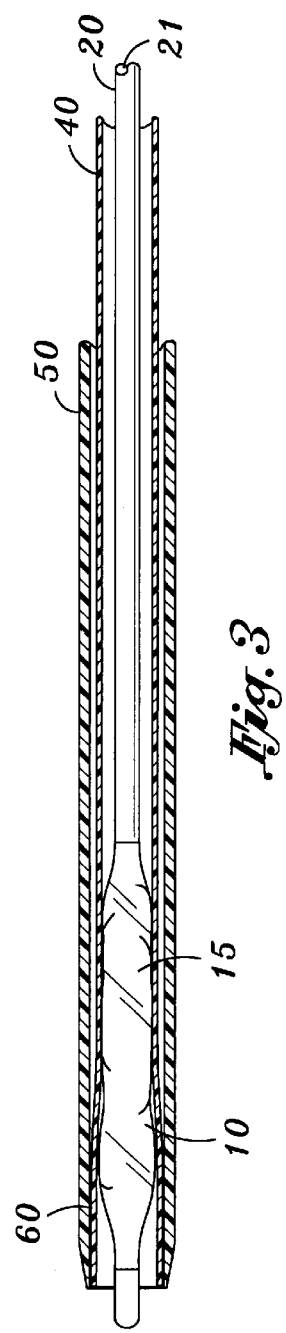

SHROUDED STRAIN RELIEF MEDICAL BALLOON DEVICE AND METHOD OF USE

BACKGROUND ART

The present invention is related to methods and apparatus for clearing blocked natural and synthetic body lumens. More specifically, this invention is related to methods and apparatus for percutaneously altering balloon configuration during clearing of blocked natural and synthetic body lumens by use of a strain relief tube, whereby the use of such balloon procedures is broadly enabled, and wherein the functional utility, ease of use, and wide applicability of the device in medical practice constitutes progress in science and the useful arts. Furthermore, the present invention teaches processes for the use of the device in medical practice.

A variety of techniques and instruments have been developed for use in the removal or repair of obstructive material in lumens such as vessels and other body passageways. Such material may include atheromas, thrombi, or emboli. An atheroma is a mass of plaque of degenerated, thickened arterial intima occurring in atherosclerosis. A thrombus is an aggregation of blood factors, primarily platelets and fibrin with entrapment of cellular elements, frequently causing vascular obstruction at the point of its formation. An embolus is a clot or other plug brought by the blood from another vessel and forced into a smaller one, thus obstructing the circulation.

Balloon catheters are finding increasing use in medical procedures such as percutaneous transluminal angioplasty, valvuloplasties, percutaneous transluminal nephrostomy, ureteral dilation, biliary duct dilation, esophageal tract dilation, cochlear canal dilation, percutaneous transluminal renal angioplasty, and the like. Balloons for use in these procedures have been prepared from a variety of polymeric materials which are blood and tissue compatible. Among those materials that have been employed include materials such as poly(vinylchloride), polyethylene and the like, homopolymers or copolymers of olefins, polyethylene/vinyl acetate copolymers, polyethylene terephthalate (PET), irradiated polyethylene, and polyurethanes.

Several problems exist with respect to the utilization of balloons in these procedures. In the past, medical device balloon materials have included balloons having a wall thickness at which the material exhibits strength and flexibility that allow inflation to a working diameter or designated initial dilation diameter which, once achieved, is not surpassable to any significant degree without balloon breakage or substantially increasing the risk of balloon breakage. Balloons of these materials can be characterized as being substantially non-distensible balloons that are not stretchable, expandable or compliant to a substantial extent beyond this working diameter. Such substantially non-distensible balloons can be characterized as being somewhat in the nature of paper bags which, once inflated to generally remove folding wrinkles, do not further inflate to any significant degree. Polymeric materials of this substantially non-distensible type that are used or proposed for use as medical balloons include polyethylene terephthalates (PET), and irradiated polyethylene.

As an example of such problems, a typical procedure in which balloons are used is percutaneous transluminal coronary angioplasty (PTCA), which is widely accepted as an effective treatment of blockages in the coronary arteries. Blockages (stenoses) may occur from cholesterol precipitation on the coronary wall, which may be in any stage from initial deposit through aged lesions. Coronary arteries can also become blocked due to formation of thrombus.

The most widely used percutaneous coronary angioplasty makes use of a dilation balloon catheter. A catheter is inserted into the patient's vascular system and guided until a balloon at the distal end of the catheter is positioned across the stenosis. The balloon of the dilation catheter must be deflated to a low profile in order for it to be passed through the guide catheter and, more particularly, through the stenosis. The balloon is deflated by applying negative pressure to the balloon through an inflation/deflation lumen that extends from the proximal end of the catheter to the interior of the balloon.

The configuration assumed by the balloon upon deflation presents a problem. Typically, the balloon forms a pair of opposed, radially-extending, flat wings, when collapsed under the influence of negative pressure, which may make passage through the lumen and particularly the obstruction difficult. A radiographic contrast fluid is then passed under pressure through an inflation lumen of the catheter to the balloon, which causes the balloon to expand outward. As the balloon expands, it dilates the lumen of the artery and compresses the stenosis. Upon being compressed, the stenosis may break up or flatten out against the arterial wall. The balloon is subsequently deflated by reducing the applied pressure and, once in its collapsed configuration, it is either withdrawn from the artery or placed across another stenosis, to restore normal blood flow through the artery.

To effectively expand the lumen and compress the stenosis, it is desirable that the balloon be reliably inflatable to a relatively large diameter when the balloon is infused with fluid. This is so in order to expand the balloon evenly within the affected artery to dilate the vessel evenly, compress, and hence compromise the stenosis. Also, it is desirable that the balloon be reliably collapsible to a minimal, radially compact cross sectional shape incident to balloon insertion and withdrawal. This is to facilitate insertion and withdrawal of the balloon in artery. While existing angioplasty balloons are collapsible, it is unfortunately the case that many existing balloons typically cannot be reliably collapsed, i.e., deflated, to a radially compact minimal cross section after inflation. Instead, they often flatten when deflated in a phenomenon known as "winging", in which the flat, lateral portions, or flaps, of the deflated balloon project laterally outward. This is deemed to be undesirable by many practitioners because of a concern that the flat wings or flaps may damage, e.g., an artery wall, as the deflated balloon is removed from the arterial system. Consequently, a flattened balloon can be relatively difficult to withdraw from an artery, because it is difficult to get large flaps to fold together and squeeze out all of the space between them.

By way of further explanation, the cross-sectional configuration assumed by a typical dilation balloon when the balloon is aspirated by applying negative pressure to the balloon interior, is a pair of diametrically opposed wings as the balloon collapses. The physician typically must manually wrap the wings about its catheter shaft, creating a low profile configuration which permits easy insertion into the lumen of a guide catheter. Difficulty may arise, following the dilation procedure, either when it is desired to withdraw the balloon catheter through the lumen of the guide catheter or when it is desired to deflate the balloon and reposition it at another vascular location to perform another dilation. In particular, the diametrically opposed wings may not wrap closely about the catheter shaft as the catheter is withdrawn back into the guide catheter or is repositioned within the arteries. Instead, the wings may catch on the distal opening of the guide catheter or may preclude reinsertion of the balloon into another stenosis.

A further problem arises in connection with a material such as polyethylene terephthalate (PET). Thus, balloons made of PET that are especially useful in medical dilation procedures have been disclosed in U.S. Pat. No. Re. 33,561 to Levy. Even though PET is advantageous from the point of view of its especially high tensile strength and its tightly-controllable inflation characteristics, it has undesirable properties as well. In some situations, biaxial orientation of polyethylene terephthalate will impart excessive crystallinity to an angioplasty balloon, or the Young's modulus will be simply too high. Under these circumstances, the balloon itself will not readily fold over and down. The resistance to folding, or "winging," is an especially difficult problem when it comes to larger balloons, such as those intended for valvuloplasty applications. A further problem encountered in using dilation balloon catheters is the failure of the balloon to deflate, following dilation of the obstruction. Because of a malfunction in the catheter itself, the dilation balloon may fail to deflate when aspirated. In these instances, the balloon must be intentionally destroyed before withdrawal through the guide catheter. The balloon is destroyed by inflating the balloon to a pressure at which the balloon wall ruptures or bursts. Unfortunately, many current dilation balloons have burst pressures which exceed the delivery capabilities of most clinical inflation devices, often requiring burst pressures in excess of 20 Bars. Such pressure may rupture the body lumen as well as the dilation balloon, thereby creating an undesirable hazard to the patient.

Also, it has been observed that thin-walled materials such as polyethylene terephthalate have a tendency to form pinholes or exhibit other signs of weakening, especially when flexed. Such a tendency can require extreme care in handling so as to avoid inadvertent damage that could substantially weaken a polyethylene terephthalate medical balloon. Although it is known that a more flexible balloon can be made by thinning the wall, such thinned polyethylene terephthalate balloons become extremely fragile and may not survive insertion through the cardiovascular system with desired integrity and without pin-holing and/or rupture.

Various balloon configurations have been proposed in the prior art for providing a dilation balloon catheter having the lowest profile as possible when deflated and the largest possible diameter when inflated. One approach, which is suggested, for example, in U.S. Pat. No. 5,087,246 to Smith and in U.S. Pat. No. 5,147,302 to Euteneuer et al., is to provide a dilation balloon having more than two flaps or wings, (for example, three wings). The ease with which such flaps fold is enhanced when their number is increased. However, this and other suggested modifications do not address further difficulties encountered in the medical use of balloons in body lumens. Numerous balloon protectors-that wrap the balloon tightly in its deflated condition to minimize the outer diameter of the balloon in its deflated state are known as recited by Jung and Sasamine in International Patent Application WO 94/07561 published Apr. 14, 1994 which is expressly incorporated herein in its entirety by reference. In contradistinction to the present invention, none of the balloon protectors recited by Jung and Sasamine are employed in deflating and withdrawing the balloon after it has been inflated, nor are they effective in determining the length of the inflated portion of the balloon.

A further difficulty encountered in the medical use of balloons in body lumens derives from the fact that the obstruction in the lumen may extend along a varying length of the lumen. For example, the obstruction may extend along less than about 1.0 cm. of the lumen or, alternatively, along more than about 1.0 cm. of the lumen. In order to clear an obstruction of say, about 3.0 cm., with about a 1.0 cm. balloon, the surgeon must successively deflate the balloon after clearing the first portion of obstruction, move the balloon forward in the lumen, and reinflate the balloon. It will be understandable from the foregoing discussion of the difficulties inherent in the inflation and deflation processes that such multiple inflation-deflation cycles are undesirable.

Balloon manufacturers have attempted to address the problem posed by the fact that the obstruction in the lumen may extend along a varying length of the lumen by producing the balloons in various lengths. For example, angioplasty balloons may be produced in a range of lengths including 1.0 cm., 2.0 cm., 3.0 cm., and the like longer lengths. However, this solution to the problem poses even further difficulties. First, the surgeon is required to estimate the length of the required balloon in advance, which may be difficult to do. Second, the fact that the manufacturer is required to produce an extensive range of balloons, and the fact that hospitals are required to stock a large inventory of balloon sizes understandably substantially increases the costs of these procedures.

Variations on the known medical use of dilation balloon systems have not been forthcoming, despite recent developments in the technology related to balloon technology. Even though balloons are used extensively in medical practice, prior devices, products, or methods available to medical practitioners have not adequately addressed the need for advanced methods and apparatus for percutaneously altering balloon configuration as set forth below.

The present invention embraces and finally addresses the clear need for advanced methods and apparatus for percutaneously altering balloon configuration. Thus, as pioneers and innovators attempt to make methods and apparatus for percutaneously altering balloon configuration cheaper, more universally used, and of higher quality, none has approached same in combination with simplicity and reliability of operation, until the teachings of the present invention. It is respectfully submitted that other references merely define the state of the art or show the type of systems that have been used to alternately address those issues ameliorated by the teachings of the present invention. Accordingly, further discussions of these references has been omitted at this time due to the fact that they are readily distinguishable from the instant teachings to one of skill in the art.

OBJECTS AND SUMMARY OF THE INVENTION

Accordingly, it is an object of the present invention to provide a device to reliably collapse a dilation balloon into a compact minimal cross sectional configuration. A further object of the present invention is to provide a device to reliably collapse a dilation balloon into a compact minimal cross sectional configuration without tearing. Another object of the present invention is to provide a device to reliably inflate only a portion of a collapsible dilation balloon into a radially-symmetrical, relatively large cross sectional configuration without tearing. It is also an object of the present invention to provide a device in which it is possible to incorporate a collapsible dilation balloon has a substantially high resistance to leaking and tearing when the balloon is inflated. A further object of the present invention to provide a device incorporating a collapsible dilation balloon which is relatively easy to use and comparatively cost-effective to manufacture. Yet a further object of this invention is to overcome the problem of "winging" using the apparatus and method of the invention. Still a further object of this invention to provide an apparatus that is suitable for use with the variety of polymeric materials that are used in dilation balloon catheterization. Yet still a further object of this invention is to provide an apparatus that eliminates the need of the manufacturer to produce an extensive range of balloon lengths. Even a further object of this invention is to provide an apparatus that eliminates the need and attendant costs for hospitals to stock a large inventory of balloon lengths. Even still a further object of this invention is to provide an apparatus that eliminates the need and attendant costs for medical practitioners to undertake multiple inflation-deflation cycles in the use of the apparatus. Even yet still a further object of this invention is to provide a method for each use of the apparatus of the invention.

These and other objects are accomplished by the parts, constructions, arrangements, combinations and subcombinations comprising the present invention, the nature of which is set forth in the following general statement, and preferred embodiments of which—illustrative of the best modes in which applicant has contemplated applying the principles—are set forth in the following description and illustrated in the accompanying drawings, and are particularly and distinctly pointed out and set forth in the appended claims forming a part hereof.

The present invention is related to methods and apparatus for clearing blocked natural and synthetic body lumens. More specifically, this invention in one aspect is related to methods and apparatus for percutaneously altering balloon configuration during clearing of blocked natural and synthetic body lumens using a dilation catheter device comprising a shroud tube of appropriate size for use in a predetermined body lumen. The shroud tube terminates at its proximal end in a handle or other fitting for moving.

The shroud tube has within it a strain relief tube adapted at its distal end to reversibly assume a flared, funnel-shape or a collapsed shape. The strain relief tube has a handle or other fitting for moving at its proximal end. The strain relief tube has an elongate flexible balloon catheter within it, wherein the balloon catheter includes a balloon fluid passage for its full length. A dilation balloon is mounted on the distal end of the balloon catheter in fluid communication with the balloon fluid lumen. The balloon fluid lumen is connected to means for applying pressure and vacuum such as pumps, pressurized gas, pressurized liquid and the like in order to alter the configuration of the balloon. Likewise, the configuration of the balloon can be altered by altering the position of contact of the strain relief tube with the balloon and by altering the pressure in the balloon fluid lumen.

The invention also includes a method for altering the configuration of an inflatable balloon to a predetermined low profile deflated configuration by means of a strain relief tube so that, after inflation to a dilation pressure, the balloon reattains the predetermined deflated configuration after deflation. The method also includes inflating the balloon to one or more of several predetermined lengths by altering the position of the strain relief tube of the invention.

The present invention is directed to a dilation catheter device comprising a shroud tube having a total preselected diameter effective for use in a preselected body lumen, including a handle, protrusion and the like for moving the shroud tube in the lumen. The shroud tube has a strain relief tube extending therethrough. The strain relief tube functions as a swage: it has a distal end adapted to reversibly form a flared, funnel-shape effective for swaging the surface of a dilation balloon, and a collapsed shape. The strain relief tube has a proximal end terminating in a handle, protrusion, and the like for moving the strain relief tube. The strain relief tube has an internal diameter sufficient to accommodate an elongate flexible balloon catheter; the balloon catheter extending therethrough. The balloon catheter has a balloon fluid lumen extending therethrough from its proximal to its distal end, and a proximal end terminating in a handle, protrusion or the like for moving the balloon catheter. A balloon is mounted on the distal end of the balloon catheter, wherein the interior of the balloon is in fluid communication with the balloon fluid lumen.

The balloon is further adapted for inflation into an inflated configuration and deflation into a collapsed configuration. The balloon has a cross section defining a first cross-sectional area when the balloon is in the inflated configuration and a second cross-sectional area smaller than the first area when the balloon is in the collapsed configuration. In one aspect, there is a stent enveloping the balloon in the collapsed configuration. The device has fluid couplings for connecting the balloon fluid lumen with means for applying pressure and vacuum; whereby the configuration of the balloon can be altered by altering the position of contact of the distal end of the strain relief tube with the surface of the balloon and by altering the pressure and the vacuum in the balloon fluid lumen.

In one aspect, distal end of the strain relief tube has longitudinal grooves in its surface, but in another aspect, the distal end of the strain relief tube has no grooves in its surface. The balloon may be made of such balloon materials as, for example, polyethylene terephthalate, high density polyethylene, irradiated polyethylene, polyamides, polycarbonates and stiff polyurethanes, polyvinyl chloride, polyethylene, polyester copolymers and polyolefin copolymers and may have a burst pressure of at least about 300 psi (2.07 MPa). In a further aspect, the balloon comprises a high molecular weight, biaxially oriented, flexible polyethylene terephthalate balloon that may have a wall tensile strength of at least about 31,714 psi (218.86 MPa). In even a further aspect, the balloon may be made of a polyethylene terephthalate homopolyester having an intrinsic viscosity of about 0.8 to about 1.1. Still other aspects of the invention include devices wherein the balloon has a wall thickness of about 0.028 to about 0.045 mm or wherein the balloon is an imperforate, inelastic balloon. Still further aspects of the invention include devices wherein the balloon is substantially porous, or may include sections of porosity as a means for the delivery of medically useful agents. Even further, the balloon material may be reinforced by fiber material.

The preselected body lumen may be a lumen for the passage of blood, bile, urine, or it may be a gastrointestinal lumen, an esophageal lumen, a cochlear canal, or a lumen for the passage of lymph. The device may include means, for example a porous balloon or a drug-eluting stent, to deliver a medically useful agent, wherein the means to deliver a medically useful agent is adapted to release a medically useful agent, for example an x-ray contrast agent, a thrombolytic agent, a viral vector agent, or an enzyme such as a proteolytic enzyme, into the body lumen continually or at a predetermined time. The release may be accomplished using pumping means such as gas pressure, mechanical pressure, and liquid pressure. The balloon fluid lumen may be adapted to contain medically useful agents such as radioactive agents and x-ray contrast agents.

In yet still another aspect the invention comprises packaging material and the dilation catheter device contained within the packaging material, wherein the device is effective for use in a preselected body lumen; and the packaging material includes a label that indicates that the device is effective for use in the preselected body lumen. In addition, the packaging material may contain at least one item selected from the group consisting of guidewires, introducers, containers, means for applying pressure and vacuum, stents, medically useful agents, medical syringes, and instructional material, for example printed materials, CD disks, magnetic data storage disks, and videotapes.

A method for using the dilation catheter device to perform a dilation procedure in a lumen (for example a lumen for the passage of blood) of a patient in need of such a procedure involves passing the strain relief tube with the collapsed balloon through the shroud tube and out the distal end of the shroud tube, inflating the balloon (for example with a fluid containing an x-ray contrast agent) to the inflated configuration to perform a dilation, deflating the balloon to the collapsed configuration while moving the balloon catheter proximally within the strain relief tube having the distal end adapted to reversibly form a flared, funnel-shape until the balloon in the collapsed configuration is fully within the strain relief tube, and, removing the dilation catheter device from the patient.

The method may be performed with a dilation catheter device that includes means for delivery of a medically useful agent, for example a porous balloon, wherein the means for delivery of a medically useful agent is adapted to release a medically useful agent into the body lumen at a predetermined time, the method further comprising the step of releasing a medically useful agent into the body lumen at a predetermined time.

The method may be performed with a dilation catheter device that includes a stent enveloping the balloon in the collapsed configuration, whereby the stent is expanded upon inflating the balloon to the inflated configuration to perform a dilation.

BRIEF EXPLANATION OF THE DRAWINGS

The foregoing and other objects and advantages of the invention will be appreciated more fully from the following further description thereof, with reference to the accompanying drawings wherein:

FIG. 1 is an elevational view of a dilation catheter device of the present invention.

FIG. 2 is an enlarged sectional illustration of the dilation catheter device of FIG. 1 as seen along lines 2—2 of FIG. 1.

FIG. 3 is a longitudinal sectional illustration of one embodiment of the invention with the balloon in a deflated configuration.

DETAILED DESCRIPTION OF THE PREFERRED EMBODIMENTS

In accordance with one embodiment of the present invention, as shown in FIGS. 1–5, a dilation balloon 10 is carried at the distal end of a balloon catheter 20. An inflation lumen 21 extends through catheter 20 from the proximal to the distal end and is in fluid communication with the interior of balloon 10. The proximal end of the catheter (not, shown) is adapted to be connected to a suitable fitting, such as a luer fitting, by which an inflation/deflation device such as a syringe may be connected. Catheter 20 may be formed from an appropriate polymeric material as will be appreciated by those familiar with the art. Balloon 10 may be formed from a polymeric material such as polyethylene terephthalate.

By way of example, in a device adapted for coronary arterial use, the balloon illustrated may have an inflated diameter of between about 1.5 mm to about 4.0 mm. The cylindrical midportion of balloon 10 may be about 2 cm long. It should be understood, however, that the invention contemplates the use of balloons other than for coronary angioplasty use in dilation procedures, and that the dimensions of such other balloons may vary from those illustrated and described herein.

The wall of balloon 10 is relatively thin. By way of example, for a balloon having an inflated diameter of about 3.0 mm, an appropriate wall thickness would be between about 0.00025 inches (0.000635 cm. to about 0.00050 inches (0.00127 cm.).

Figure 5:
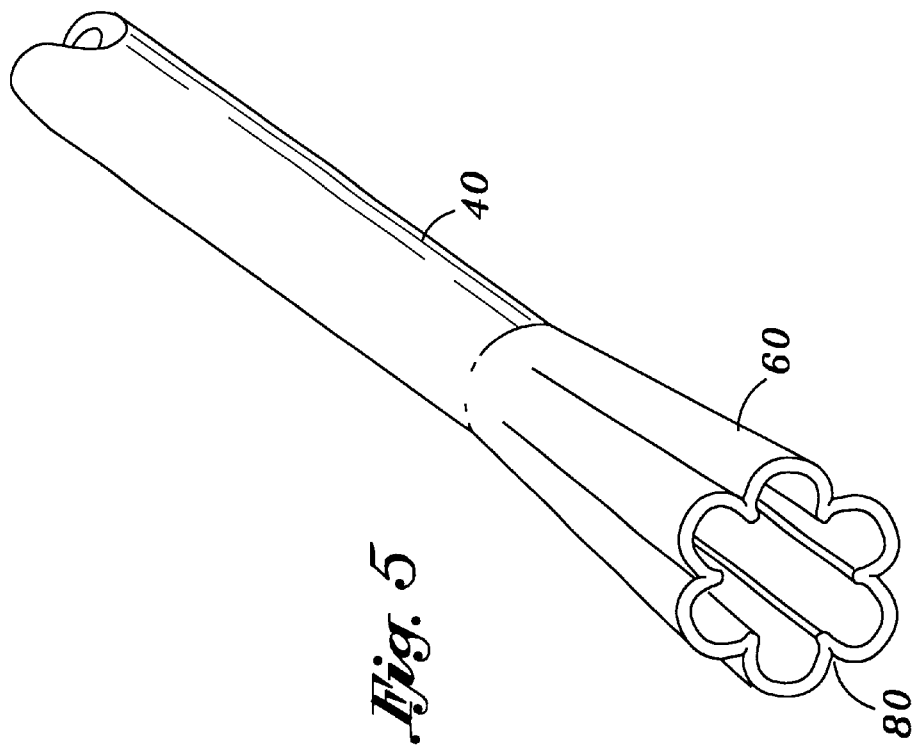
FIG. 5 is a perspective view of one embodiment of the invention with the distal end of the strain relief tube in the form of a collapsed shape having longitudinal grooves in its surface.
Figure 4:
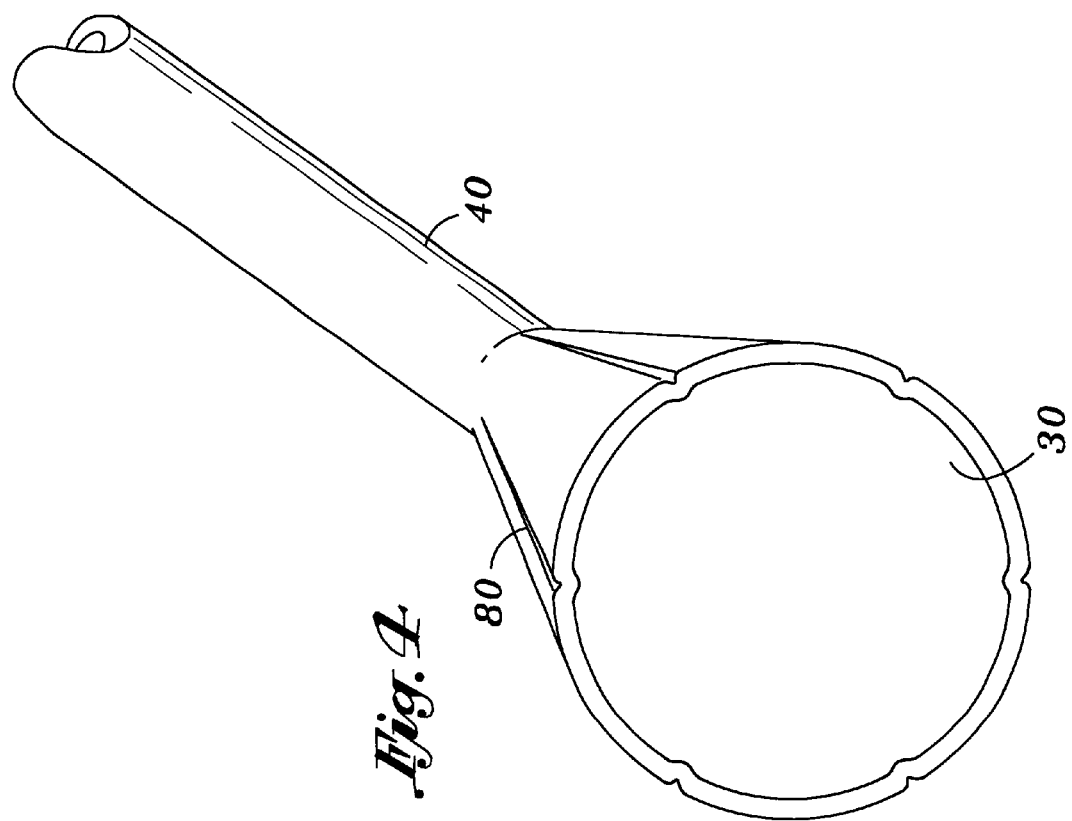
FIG. 4 is a perspective view of one embodiment of the invention with the distal end of the strain relief tube in the form of a flared, funnel-shape.

As shown in FIG. 2, catheter 20 passes through a strain relief tube 40. Tube 40 has a distal end that can reversibly assume a funnel-shaped configuration 30, as shown generally shown in FIG. 4, and a collapsed configuration 60 as generally shown in FIG. 5. As shown in FIG. 4, end 30 has a plurality of circumferentially spaced lines 80 of reduced wall thickness. Lines 80 extend longitudinally of end 30, as shown in FIG. 4.

Tube 40 passes through a shroud tube 50. Tubes 40 and 50 may be formed from an appropriate polymeric material as will be appreciated by those familiar with the art.

In a typical procedure to perform a dilation procedure in a lumen (for example a lumen for the passage of blood) of a patient in need of such a procedure, the physician begins with dilation catheter device in the configuration generally shown in FIG. 3. Here, balloon 10 is in a collapsed configuration 15 and is situated entirely within end 30 of tube 40. Tube 40 is situated entirely within shroud tube 50. The physician passes tube 50 in this configuration into the area for dilation. To perform a dilation, the typical procedure next involves passing tube 20 with balloon 10 out the distal end of tube 40, while simultaneously inflating some or all of balloon 10 (for example with a pressurized fluid containing an x-ray contrast agent) to the inflated configuration generally shown in FIG. 2. Following this step, deflation of balloon 10 to the collapsed configuration 15 is accomplished by reducing pressurization while moving catheter 20 proximally within tube 40. The smooth collapse of the balloon is made possible by the swaging action of distal end 30 which forms a flared, funnel-shape. When balloon 10 in collapsed configuration 15 is fully within tube 40, tube 40 is moved proximally back into tube 50, causing end 30 to reassume its collapsed shape 60 as shown in FIG. 3 and FIG. 5. The physician may then reposition the device for further dilation, or for removing the dilation catheter device from the patient.

The reduced profile 15 assumed by balloon 10 upon passage through distal end 30 in its flared, funnel-shaped configuration in this procedure substantially reduces the chance of damage to the balloon wall upon withdrawal. It increases the ability of the deflated balloon to pass through tight stenoses. The reduced profile of balloon 10 prevents the balloon from being caught at the distal end of a guide catheter.

Presently, if a balloon does not deflate when desired, a practitioner may over inflate the balloon to intentionally rupture the balloon wall, causing immediate deflation of the balloon and enabling withdrawal of the balloon from the lumen. A balloon may have a minimum burst pressure of more than about 20 Bar, which can cause injury to the patient. Deflation of the balloon 10 in the present invention can always be accomplished reliably by the method just outlined. Thus it will be appreciated that the invention provides a new and improved dilation catheter device by which the balloon may be more readily contracted to a low profile. It should be understood, however, that the foregoing description of the invention is intended merely to be illustrative thereof and that other modifications in embodiments may be apparent to those skilled in the art without departing from its spirit. For example, whereas the invention has been illustrated in connection with a coronary dilation catheter, it may be used with other balloon catheters such as a peripheral blood vessel dilation catheter, an esophageal catheter, or a cochlear canal catheter. Additionally, although the illustrative embodiment has been described in connection with a balloon made from polyethylene terephthalate, which is relatively inelastic, (non-compliant), the invention also may be incorporated in balloons formed from more compliant materials, such as polyvinyl chloride or polyethylene.

On this basis, the instant invention should be recognized as constituting progress in science and the useful arts, as solving the problems in cardiology enumerated above. In the foregoing description, certain terms have been used for brevity, clearness and understanding, but no unnecessary limitation are to be implied therefrom beyond the requirements of the prior art, because such words are used for descriptive purposes herein and are intended to be broadly construed.

Having described preferred embodiments of the invention with reference to the accompanying drawings, it is to be understood that the invention is not limited to those precise embodiments, and that the various changes and modifications may be effected therein by one skilled in the art without departing from the scope or spirit of the invention s defined in the appended claims. For example, the product can have other shapes, or could make use of other metals and plastics. Thus, the scope of the invention should be determined by the appended claims and their legal equivalents, rather than by the examples given. All changes that come within the meaning and range of equivalency of the claims are to be embraced within their scope.

DEFINITIONS

Unless defined otherwise, all technical and scientific terms used herein have the same meaning as is commonly understood by one of skill in the art to which this invention belongs. All patents and publications referred to herein are incorporated in their entirety by reference.

As used herein, a shrouded strain relief medical balloon device is a device that is capable of producing inflated balloon configurations of varying lengths from a given balloon by altering the position of contact of the distal end of a strain relief tube with the surface of the balloon.

As used herein, a "swage" is any device that can shape cold metal or plastic.

As used herein, "swaging" refers to the process of bending, shaping or tapering a metal or plastic object.

As used herein, a "funnel" is a tube having a conical shape.

As used herein, a "funnel-shaped end" is a flared end that looks like a funnel.

As used herein, a "medically useful agent" is any substance, or any formulation of a substance, that can be used for any diagnostic or therapeutic medically useful purpose, or in any diagnostic or therapeutic medically useful procedure.

As used herein, the term "wings" refers to the pair of opposed, radially extending, flat structures formed by an ordinary cylindrical dilation balloon when collapsed under the influence of negative pressure.

As used herein, the terms "dilation" and "dilatation" are synonymous.

What is claimed is:

1. A dilation catheter device comprising, in combination:
   a shroud tube having a total preselected diameter effective for use in a preselected body lumen, said shroud tube including a means for moving said shroud tube in said lumen;
   said shroud tube having a strain relief tube extending therethrough;
   said strain relief tube having:
      a distal end adapted to reversibly form a flared, funnel-shape and a collapsed shape for contacting the surface of a dilation balloon;
      a proximal end terminating in means for moving said strain relief tube;
      an internal diameter sufficient to accommodate an elongate flexible balloon catheter; said balloon catheter extending therethrough;
   said balloon catheter having:
      a balloon fluid lumen extending therethrough from its proximal to its distal end;
      a proximal end terminating in means for moving said balloon catheter;
      a balloon mounted on said distal end of said balloon catheter, wherein:
         the interior of said balloon is in fluid communication with said balloon fluid lumen;
         said balloon is further adapted for inflation into an inflated configuration and deflation into a collapsed configuration;
         said balloon has a cross section defining a first cross-sectional area when said balloon is in said inflated configuration and a second cross-sectional area smaller than said first area when said balloon is in-said collapsed configuration; and,
   means for connecting said balloon fluid lumen with means for applying pressure and vacuum;
   whereby said configuration of said balloon can be altered by altering the position of contact of said distal end of said strain relief tube with said surface of said balloon and by altering said pressure and said vacuum in said balloon fluid lumen.

2. The device of claim 1 wherein said distal end of said strain relief tube has longitudinal grooves in its surface.

3. The device of claim 1 wherein said balloon is made of a balloon material selected from the group consisting of polyethylene terephthalate, high-density polyethylene, irradiated polyethylene, polyamides, polycarbonates and stiff polyurethanes, polyvinyl chloride, polyethylene, polyester copolymers and polyolefin copolymers.

4. The device of claim 1 wherein said balloon comprises a high molecular weight, biaxially oriented, flexible polyethylene terephthalate balloon.

5. The device of claim 1 wherein said balloon comprises a high molecular weight, biaxially oriented, flexible polymeric balloon having a wall tensile strength of at least about 31,714 psi (218.86 MPa).

6. The device of claim 1 wherein said balloon has a burst pressure of at least about 300 psi (2.07 MPa).

7. The device of claim 3 wherein said polyethylene terephthalate is a polyethylene terephthalate homopolyester having an intrinsic viscosity of about 0.8 to about 1.1.

8. The device of claim 3 wherein said balloon has a wall thickness of about 0.028 to about 0.045 mm.

9. The device of claim 1 wherein said balloon is an imperforate, inelastic balloon.

10. The device of claim 1 wherein said balloon material is reinforced by fiber material.

11. The device of claim 1 wherein said preselected body lumen is a lumen for the passage of blood.

12. The device of claim 1 wherein said preselected body lumen is a lumen for the passage of bile.

13. The device of claim 1 wherein said preselected body lumen is a lumen for the passage of urine.

14. The device of claim 1 wherein said preselected body lumen is a gastrointestinal lumen.

15. The device of claim 1 wherein said preselected body lumen is selected from the group consisting of esophageal lumens and cochlear canals.

16. The device of claim 1 wherein said preselected body lumen is a lumen for the passage of lymph.

17. The device of claim 1, further including means to deliver a medically useful agent, wherein said means to deliver a medically useful agent is adapted to release a medically useful agent into said body lumen.

18. The device of claim 17, wherein said release is accomplished using pumping means.

19. The device of claim 18, wherein said pumping means is selected from the group consisting of gas pressure, mechanical pressure, and liquid pressure.

20. The device of claim 17, wherein said medically useful agent is an x-ray contrast agent.

21. The device of claim 17, wherein said medically useful agent is a thrombolytic agent.

22. The device of claim 17, wherein said medically useful agent is a viral vector agent.

23. The device of claim 17, wherein said medically useful agent is an enzyme.

24. The device of claim 23, wherein said enzyme is a proteolytic enzyme.

25. The device of claim 1, wherein said balloon fluid lumen is adapted to contain a medically useful agent.

26. The device of claim 25, wherein said medically useful agent is selected from the group consisting of radioactive agents and x-ray contrast agents.

* * * * *